United States Patent [19]

Uematsu et al.

[11] 4,349,554
[45] Sep. 14, 1982

[54] METHOD OF USING CARBOSTYRIL DERIVATIVES AS PLANT FUNGICIDES

[75] Inventors: Tamon Uematsu, Toyonaka; Satoru Inoue, Nishinomiya; Norihisa Yamashita, Takarazuka, all of Japan

[73] Assignee: Sumitomo Chemical Company, Limited, Japan

[21] Appl. No.: 152,430

[22] Filed: May 22, 1980

Related U.S. Application Data

[63] Continuation of Ser. No. 866,395, Dec. 30, 1977, abandoned.

[30] Foreign Application Priority Data

Jan. 18, 1977 [JP] Japan ................................. 52-4769
Aug. 16, 1977 [JP] Japan ................................ 52-98386
Aug. 17, 1977 [JP] Japan ................................ 52-98965

[51] Int. Cl.³ ..................... A61K 31/47; C07D 215/22
[52] U.S. Cl. ................................. 424/258; 546/157; 546/158
[58] Field of Search ................. 546/157, 158; 424/258

[56] References Cited

U.S. PATENT DOCUMENTS 3,836,657 9/1974 Sharp ............................. 260/289 R
3,879,553 4/1975 Tobol ................................. 424/258

OTHER PUBLICATIONS

Howitz et al., Annalon, vol. 396, p. 59, cited in Beilstein's Hand. der Orgchem. Band 21, 41st Erg. p. 297 (1935).
Mayer et al., "Berichte", 60, pp. 858–864 (1927).

Primary Examiner—David B. Springer
Attorney, Agent, or Firm—Wenderoth, Lind & Ponack

[57] ABSTRACT

A fungicidal composition which comprises as an active ingredient a 1,8-disubstituted carbostyril derivative of the formula:

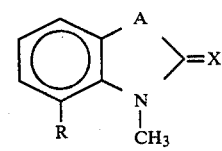

wherein R is a chlorine, bromine or fluorine atom or methyl group, A is an ethylene or vinylene group and X is an oxygen or sulfur atom, and an inert carrier or diluent.

12 Claims, No Drawings

METHOD OF USING CARBOSTYRIL DERIVATIVES AS PLANT FUNGICIDES

This is a continuation of application Ser. No. 866,395, filed Dec. 30, 1977 now abandoned.

The present invention relates to a fungicidal composition which comprises as an active ingredient a 1,8-disubstituted carbostyril derivative of the formula:

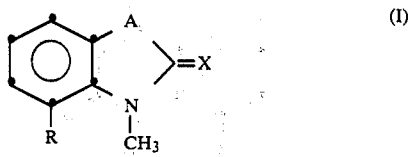

wherein R is a chlorine, bromine or fluorine atom or methyl group (preferably chlorine atoms or methyl group), A is an ethylene or vinylene group and X is an oxygen or sulfur atom (preferably oxygen atom), and an inert carrier, and their preparation and use as fungicide.

It is already well known that some of carbostyril derivatives have an antimicrobial activity on certain microorganisms (U.S. Pat. Nos. 3,836,657 and 3,879,553 and Japanese Patent Publication (unexamined) No. 50136/1974). Further, 1,8-dimethylcarbostyril is per se known (J. Org. Chem., vol. 37, No. 26, 4410-15 (1972)). However, the fungicidal activity of this compound is not referred to in the literature. As the results of the extensive study, it has now been found that the 1,8-disubstituted carbostyril derivatives (I) exhibit an antimicrobial activity which is widely applicable and markedly superior as compared with their homologues against phytopathogenic microorganisms which do a great damage to cultivation of rice plant, for example on rice blast fungus, sheath blight fungus, stem-rot fungus, helminthosporium leaf spot fungus, and in addition show no material phytotoxicity to plants and extremely low toxicity to warm-blooded animals and fishes and hardly remain in the body of crops.

The 1,8-disubstituted carbostyril derivatives (I) are especially effective in controlling rice blast (*Pyricularia oryzae*) which is serious disease of rice, they have a property to be applicable by any of the three application techniques of foliar application, submerged application and soil application, and further that they have a high controlling effect. Also, they have volatility which can be made use for the application of it. Furthermore, the 1,8-disubstituted carbostyril derivatives (I) possess a very strong effect with such rapidity and long persistency that can not be obtained from the well-known foliar-applied, water-surface-applied and soil-applied fungicides for rice blast.

The 1,8-disubstituted carbostyril derivatives (I) of the present invention structurally relate to some of the compounds disclosed in U.S. Pat. Nos. 3,836,657 and 3,879,553 and Japanese Patent Publication (unexamined) No. 50136/1974, but their effectivenesses in controlling the said disease are far superior to those of the latter compounds, and the 1,8-disubstituted carbostyril derivatives (I) are still effective with the application at lower dosages. This indicates that substitution with specific substituents at both 1- and 8-positions of carbostyril derivatives resulted in marked increase in their fungitoxic activities.

The present inventors are the first to point out this unexpected increase of activity.

A main object of the present invention is to provide the fungicidal composition containing as an active ingredient a 1,8-disubstituted carbostyril derivative (I), which is useful as fungicide.

Another object of this invention is to provide a method for preparing such composition, a method of controlling fungi and use as fungicide. A further object of the invention is to provide novel 1,8-disubstituted carbostyril derivatives of the formula;

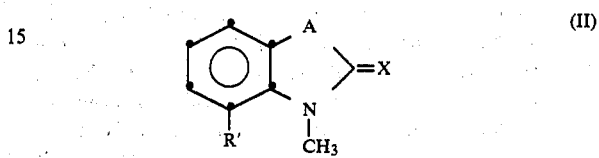

wherein X is an oxygen or sulfur atom, A is an ethylene or vinylene group, R' is a chlorine, bromine or fluorine atom or a methyl group; provided that R' is a chlorine, bromine or fluorine atom when X is an oxygen atom and A is a vinylene group, and their preparation. These and other objects and advantages of the invention will become apparent from the foregoing and subsequent descriptions.

The 1,8-disubstituted carbostyril derivatives (I) of the present invention may be prepared by various methods, of which typical examples will be described below.

Procedure A

The 1,8-disubstituted carbostyril of the formula;

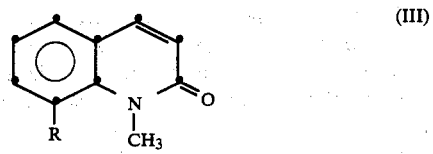

wherein R is as defined above, can be prepared by methylating an 8-substituted quinoline of the formula;

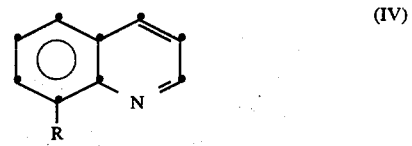

wherein R is as defined above, with a methylating agent (e.g. methyl bromide, dimethyl sulfate, methyl iodide) at a temperature from 0° C. to 100° C. in the presence or absence of an inert solvent (e.g. water, ethanol, methanol, benzene, toluene, xylene, acetone, diethyl ether, tetrahydrofuran, dioxane, or a mixture thereof) for 0.5 to 10 hours to obtain a corresponding quaternary salt, and then oxidizing the salt with an oxidizing agent (e.g. sodium ferricyanide, potassium ferricyanide) in the presence of a base (e.g. sodium hydroxide, potassium hydroxide) in an inert solvent (e.g. water, ethanol, methanol, dioxane or a mixture thereof) at a temperature below 50° C. for 0.5 to 30 hours.

Procedure B

The 1,8-disubstituted carbostyril (III) can be prepared by methylating a corresponding 1-unsubstituted carbostyril of the formula:

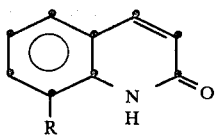

(V)

wherein R is as defined above, with a methylating agent (e.g. methyl iodine, dimethyl sulfate) at a temperature from 0° C. to 140° C. in an inert solvent (e.g. methanol, ethanol, benzene, toluene, xylene, tetrahydrofuran, dioxane, diethyl ether, water, a mixture thereof) in the presence of a base (e.g. potassium tert-butoxide, sodium ethoxide, sodium methoxide, sodium hydride, sodium hydroxide, potassium hydroxide) for 0.5 to 10 hours.

Procedure C

The 1,8-disubstituted dihydrocarbostyril of the formula:

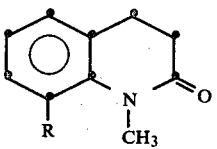

(VI)

wherein R is as defined above, can be prepared by reducing the corresponding 1,8-disubstituted carbostyril (III) with hydrogen at a temperature from 0° C. to 250° C. at atmospheric pressure or under pressure in an inert solvent (e.g. methanol, ethanol, acetic acid, dioxane, diethyl ether, water, benzene, cyclohexane, methylcyclohexane, tetrahydrofuran, ethyl acetate, ethylene glycol, or a mixture thereof) in the presence of a catalyst (e.g. Raney nickel, Raney copper, reduced copper, palladiumcarbon, colloidal palladium, colloidal rhodium, platinum oxide), and then removing the catalyst by filtration and the solvent removal by evaporation.

Procedure D

The 1,8-disubstituted dihydrocarbostyril (VI) can be prepared by methylating a corresponding 1-unsubstituted dihydrocarbostyril of the formula;

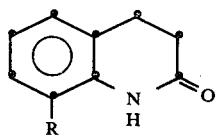

(VII)

wherein R is as defined above, with a methylating agent (e.g. dimethyl sulfate, methyl bromide, methyl iodide) at a temperature from 0° C. to 140° C. in an inert solvent (e.g. methanol, ethanol, benzene, toluene, xylene, tetrahydrofuran, dioxane, diethyl ether, water or a mixture thereof) in the presence of a base (e.g. potassium tert.-butoxide, sodium ethoxide, sodium methoxide, sodium hydroxide, sodium hydroxide, potassium hydroxide) for 0.5 to 10 hours.

Procedure E

The 1,8-disubstituted dihydrocarbostyril (VI) can be prepared by reacting a halopropionanilide of the formula;

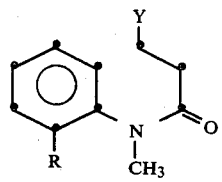

(VIII)

wherein Y is a halogen atom (e.g. bromine, chlorine, iodine) and R is as defined above, with a Lewis acid catalyst (e.g. aluminum chloride, iron chloride, tin chloride, zinc chloride) at a temperature from 25° C. to 250° C. in the presence or absence of an inert solvent (e.g. chloroform, benzene, toluene, xylene, carbon tetrachloride, carbon disulfide, chlorobenzene, dichlorobenzene, nitrobenzene) for 0.5 to 10 hours.

Procedure F

The 1,8-disubstituted carbostyril derivative of the formula;

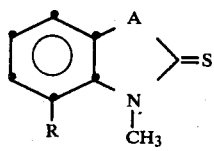

(IX)

wherein R and A are defined above, can be prepared by heating a 1,8-disubstituted carbostyril derivative of the formula;

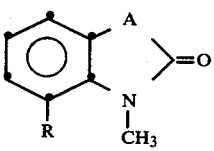

(X)

wherein R and A are as defined above, and phosphorus pentasulfide together in a suitable solvent (e.g. benzene, toluene, xylene, chloroform, carbon tetrachloride, pyridine, or a mixture thereof) at a temperature from 60° to 140° C. for 1 to 10 hours followed by filtration and solvent removal by evaporation.

The 1,8-disubstituted carbostyril derivatives (I) thus produced may be purified, if necessary, by a conventional procedure such as recrystallization, distillation and column chromatography.

The starting materials are obtainable, for instance, by the method as described in T. Kametani et al., Chem. Pharm. Bull. 15(12) 1910–1915 (1967).

Specific examples of the 1,8-disubstituted carbostyril derivatives (I) thus prepared are shown in Table 1.

TABLE 1

| Procedure | Compound No. | Chemical structure | M.p. (°C.) $n_D$ | Calcd. (%) C | H | N | Halogen | Found (%) C | H | N | Halogen |
|---|---|---|---|---|---|---|---|---|---|---|---|
| A | 1 | (8-CH₃, N-CH₃ quinolin-2(1H)-one) | m.p. 99–100° C. | 76.27 | 6.41 | 8.08 | | 76.09 | 6.34 | 8.21 | |
| A | 2 | (8-Cl, N-CH₃) | m.p. 129° C. | 62.03 | 4.17 | 7.28 | 18.31 | 62.11 | 4.30 | 7.24 | 18.22 |
| B | 3 | (8-Br, N-CH₃) | m.p. 106–107° C. | 50.44 | 3.39 | 5.88 | 33.56 | 50.29 | 3.18 | 5.66 | 33.62 |
| B | 4 | (8-F, N-CH₃) | m.p. 122° C. | 67.78 | 4.56 | 7.90 | | 67.59 | 4.33 | 7.72 | |
| C | 5 | (8-CH₃, N-CH₃ dihydro) | $n_D^{24.0}$ 1.5714 | 75.39 | 7.49 | 7.99 | | 75.41 | 7.34 | 8.03 | |
| E | 6 | (8-Cl, N-CH₃ dihydro) | m.p. 89° C. | 61.39 | 5.16 | 7.16 | 18.12 | 61.11 | 5.20 | 7.19 | 18.12 |
| D | 7 | (8-Br, N-CH₃ dihydro) | m.p. 121–122° C. | 50.02 | 4.21 | 5.83 | 33.28 | 50.13 | 4.32 | 5.90 | 33.19 |
| E | 8 | (8-F, N-CH₃ dihydro) | m.p. 72–73° C. | 67.02 | 5.64 | 7.81 | 10.60 | 67.14 | 5.57 | 7.80 | 10.62 |
| F | 9 | (8-CH₃, N-CH₃, C=S) | m.p. 102° C. | 69.79 | 5.87 | 7.40 | | 69.90 | 5.84 | 7.37 | |

TABLE 1-continued

| Procedure | Compound No. | Chemical structure | M.p. (°C.) $n_D$ | Calcd. (%) C | H | N | Halogen | Found (%) C | H | N | Halogen |
|---|---|---|---|---|---|---|---|---|---|---|---|
| F | 10 | (8-Cl, N-CH₃ carbostyril) | m.p. 120–121° C. | 57.27 | 3.85 | 6.68 | 16.91 | 57.33 | 3.75 | 6.64 | 16.89 |
| F | 11 | (8-Br, N-CH₃ carbostyril) | m.p. 108–109° C. | 47.25 | 3.18 | 5.51 | 31.44 | 47.09 | 3.20 | 5.63 | 31.55 |
| F | 12 | (8-F, N-CH₃ carbostyril) | m.p. 133–134° C. | 62.15 | 4.18 | 7.24 | 9.83 | 62.33 | 4.31 | 7.24 | 9.90 |
| F | 13 | (8-CH₃, N-CH₃ carbostyril) | $n_D^{24.5}$ 1.6634 | 69.06 | 6.86 | 7.32 | | 69.17 | 6.92 | 7.44 | |
| F | 14 | (8-Cl, N-CH₃ dihydrocarbostyril) | m.p. 74–75° C. | 56.73 | 4.77 | 6.61 | 16.74 | 56.82 | 4.76 | 5.59 | 16.75 |
| F | 15 | (8-Br, N-CH₃ dihydrocarbostyril) | m.p. 118–119° C. | 46.88 | 3.94 | 5.47 | 31.19 | 46.73 | 3.95 | 5.51 | 31.21 |
| F | 16 | (8-F, N-CH₃ dihydrocarbostyril) | m.p. 73–74° C. | 61.51 | 5.17 | 7.17 | 9.73 | 61.44 | 5.21 | 7.30 | 9.85 |

Practical and presently preferred embodiments of the preparation of the 1,8-disubstituted carbostyril derivatives (I) are illustratively shown in the following examples.

EXAMPLE 1

(Procedure A)

4.7 g. of dimethyl sulfate was added dropwise to 6.0 g. of 8-chloroquinoline at room temperature. The mixture was kept stirring at 100° C. for 3 hours, ice-cooled, and diluted with 10 ml. of water to make a solution. Thereafter, a solution of 7.4 g. of sodium hydroxide in 11 ml. of water, and a solution of 25.9 g. of potassium ferricyanide in 48 ml. of water were added to the solution at the same time at below 10° C. After stirring at room temperature for 5 hours, the precipitated crystals were filtered, washed with water, dried and recrystallized from ethanol to obtain 6.8 g. of 8-chloro-1-methylcarbostyril (m.p. 129° C.).

EXAMPLE 2

(Procedure B)

One gram of sodium hydroxide was dissolved in 15 ml. of methanol, and 4.5 g. of 8-bromocarbostyril was added to the solution at room temperature. Thereafter, 2.6 g. of dimethyl sulfate was added dropwise thereto. The reaction mixture was boiled for 3 hours, cooled to room temperature and poured into 50 ml. of water. The precipitated crystals were filtered, dried and recrystallized from ethanol to obtain 3.9 g. of 8-bromo-1-methylcarbostyril (m.p. 106°-107° C.).

EXAMPLE 3

(Procedure C)

2.0 g. of 1,8-dimethylcarbostyril was dissolved in 100 ml. of ethanol, and 250 mg. of 10% palladiumcarbon was added thereto. Thereafter, hydrogen gas was introduced into the reaction mixture at room temperature under atmospheric pressure for 10 hours while shaking the reaction mixture. After the reaction was finished, the reaction mixture was filtered to remove the catalyst, and ethanol was removed under reduced pressure to obtain 2.0 g. of 1,8-dimethyl-3,4-dihydrocarbostyril ($n_D^{24.0}$1.5714).

EXAMPLE 4

(Procedure D)

2.3 g. of 8-bromo-3,4-dihydrocarbostyril and 0.6 g. of potassium hydroxide were dissolved in 15 ml. of methanol, and 1.3 g. of dimethyl sulfate was added dropwise thereto at room temperature. Thereafter, the reaction mixture was stirred at 80° C. for 3 hours, poured into 50 ml. of water and extracted with three 30-ml portions of chloroform. The extract was dried over magnesium sulfate and filtered, and chloroform was removed under reduced pressure to obtain 1.7 g. of 1-methyl-8-bromo-3,4-dihydrocarbostyril (m.p. 121°-122° C.).

EXAMPLE 5

(Procedure E)

5.0 g. of N-methyl H-(3-chloropropionyl)-o-chloroaniline and 4.3 g. of aluminum chloride were mixed, and the mixture was gradually heated and stirred at 225° C. for 3 hours. Thereafter, the reaction mixture was allowed to cool to 60° C. and poured into 100 ml. of ice water. The precipitated crystals were filtered, dried and recrystallized from n-hexane to obtain 3.8 g. of 8-chloro-1-methyl-3,4-dihydrocarbostyril (m.p. 89° C.).

EXAMPLE 6

(Procedure F)

1.0 g. of 1,8-dimethylcarbostyril and 0.27 g. of phosphorus pentasulfide were thoroughly mixed, and stirred in 3 ml. of a dry xylene at 140° C. for 3 hours. The reaction mixture was then filtered hot through celite and washed with hot xylene. The solvent was removed from the filtrate under reduced pressure and the crystals obtained were recrystallized from n-hexane to obtain 0.85 g. of 1,8-dimethylcarbostyril-2-thione (m.p. 102° C.).

EXAMPLE 7

(Procedure F)

1.2 g. of 1-methyl-8-chloro-3,4-dihydrocarbostyril and 0.27 g. of phosphorus pentasulfide were thoroughly mixed, and stirred in 5 ml. of a dry xylene at 140° C. for 4 hours. The reaction mixture was then filtered hot through celite and washed with hot xylene. The solvent was removed from the filtrate under reduced pressure and the crystals obtained were recrystallized from ethanol to obtain 1.0 g. of 1-methyl-8-chloro-3,4-dihydrocarbostyril-2-thione (m.p. 74°-75° C.).

In the actual application as a fungicide, the 1,8-disubstituted carbostyril derivatives (I) may be used alone without incorporation of any other ingredient such as a carrier or a diluent, but for easier application, are used in any of ordinarily adopted forms such as, for example, dusts, wettable powders, oil sprays, aerosols, tablets, emulsifiable concentrates, granules and fine granules. In order to formulate these preparations, the 1,8-disubstituted carbostyril derivatives (I) may be admixed with such solid carriers or diluents as mineral powders (e.g. talc, bentonite, montomorillonite, clay, kaolin, diatomaceous earth, mica, apatite, vermiculite, gypsum, calcium carbonate, pyrophyllite, sericite, pumice, sulfur, active carbon, slaked lime), plant powders (e.g. soybean, wheat, wood, walnut shell, saw dust, bran, bark, plant extract residue, tobacco, starch, crystalline cellulose), polymeric material powders (e.g. petroleum resin, polyvinyl chloride, dammar gum, ketonic resin), fiber products (e.g. paper, corrugated cardboard, old rags), chemical fertilizers (e.g. ammonium sulfate, ammonium phosphate, ammonium nitrate, urea, ammonium chloride), alumina or wax, or with such liquid carriers or diluents as alcohols (e.g. methanol, ethanol, ethylene glycol, benzyl alcohol), aromatic hydrocarbons (e.g. benzene, toluene, xylene, methylnaphthalene), aliphatic hydrocarbons (e.g. kerosene, hexane), chlorinated hydrocarbons (e.g. chloroform, carbon tetrachloride, monochlorobenzene), ethers (e.g. diethyl ether, dioxane, tetrahydrofuran, ethylene glycol ethyl ether), ketones (e.g. acetone, methyl ethyl ketone, cyclohexanone), esters (e.g. ethyl acetate, butyl acetate, ethylene glycol acetate), acid amides (e.g. N,N-dimethylformamide), nitriles (e.g. acetonitrile) or sulfoxides (e.g. dimethylsulfoxide). If necessary, other additives such as binding and/or dispersing agent (e.g. gelatin, casein, sodium alginate, CMC, starch, gum arabic powder, lignosulfonate, bentonite, polyoxypropyleneglycol ether, polyvinyl alcohol, pine oil, liquid or solid paraffine), stabilizer (e.g. isopropyl phosphate, tricresyl phosphate, tall oil, epoxidized oil, surfactant, fatty acid, fatty acid ester) or emulsifier (e.g. alkyl sulfonate, polyoxyethylene alkyl sulfate, alkyl arylsulfonate, polyethylene glycol alkyl ether, polyoxyethylene alkyl aryl ether), wetting agent (e.g. dodecyl benzenesulfonate, lauryl sulfate), may be incorporated into the preparations. Further, the preparations may include extending agents as conventionally employed and/or other fungicides such as, for example, N-(3,5-dichlorophenyl)-1,2-dimethylcyclopropane-1,2-dicarboximide, S-n-butyl S'-p-tert-butylbenzyl N-3-pyridyldithiocarbonimidate, O,O-dimethyl O-2,6-dichloro-4-methylphenyl phosphorothioate, methyl N-benzimidazol-2-yl-N-(butylcarbamoyl)carbamate, N-trichloromethylthio-4-cyclohexene-1,2-dicarboximide, cis-N-(1,1,2,2-tetrachloroethylthio)-4-cyclohexene-1,2-dicarboximide, Polyoxin, Streptomycin, zinc ethylene-bis(dithiocarbamate), zinc dimethylthiocarbamate, manganese ethylene-bis(dithiocarbamate), bis(-dimethylthiocarbamoyl)disulfide, tetrachloroisophthalonitrile, 8-hydroxyquinoline, dodecylguanidine acetate, 5,6-dihydro-2-methyl-1,4-oxathione-3-carboxanilide, N'-dichlorofluoromethylthio-N,N-dimethyl-N'-phenylsulfamide, 1-(4-chlorophenoxy)-3,3-dimethyl-1-(1,2,4-triazol-1-yl)-2-butanone, 1,2-bis(3-methoxycarbonyl-2-thio-ureido)benzene and the like; and the 1,8-disubstituted carbostyril derivatives (I) may also be used in admixture with insecticides such as, for example, O,O-dimethyl O-4-nitro-m-tolyl phosphorothioate, O-p-cyanophenyl O,O-dimethyl phosphorothioate, O-p-cyanophenyl O-ethylphenyl phosphonothioate, O,O-dimethyl S-N-methylcarbamoylmethyl phosphorodithioate, 2-methoxy-4H-1,3,2-benzodioxaphosphorine-2- sulfide, O,O-dimethyl S-1-ethoxycarbonyl-1-phenylmethyl phosphorodithioate, α-cyano-3-phenoxybenzyl 2-(4-chlorophenyl)isovalerate, 3-phenoxybenzyl 2,2-dimethyl-3-(2,2-dichlorovinyl)cyclopropanecarboxylate, 3-phenoxybenzyl chrysanthemate and the like; and, in every case, no controlling effects of individual chemicals are decreased. Accordingly, simultaneous control of two or more injurious fungi and insencts is possible. In addition thereto, they may be used in admixture with such agricultural chemicals as nematocides and miticides and with fertilizers.

The foregoing preparations generally contain 0.1 to 95.0% by weight, preferably 0.2 to 90.0% by weight of the active ingredient (including other ingredient mixed). A suitable amount of the preparations applied is generally 10 g. to 1000 g./10 are, and the concentration of the preparations applied is preferably within the range of 0.001 to 0.1% by weight. Since, however, the amount and concentration depend upon the preparation forms, application times, application methods, application sites, diseases and crops, they may be properly increased or decreased irrespective of the aforesaid ranges.

Practical embodiments of the fungicidal composition according to the present invention are illustratively shown in the following examples, wherein parts and % are by weight.

Preparation Example 1

Dust

2 Parts of the compound (1) and 98 parts of clay were thoroughly pulverized and mixed together to obtain a dust containing 2% of the active ingredient. In application, the dust was dusted as such.

Preparation Example 2

Dust

3 Parts of the compound (2) and 97 parts of talc were thoroughly pulverized and mixed together to obtain a dust containing 3% of the active ingredient. In application, the dust was dusted as such.

Preparation Example 3

Wettable powder

50 Parts of the compound (5), 2.5 parts of a wetting agent of the dodecylbenzenesulfonate, 2.5 parts of a dispersing agent of the sodium lignosulfate and 45 parts of diatomaceous earth were thoroughly pulverized and mixed together to obtain a wettable powder containing 50% of the active ingredient. In application, the wettable powder was diluted with water, and the resulting solution was sprayed.

Preparation Example 4

Emulsifiable concentrate

10 Parts of the compound (6), 40 parts of dimethyl sulfoxide, 40 parts of xylene and 10 parts of an emulsifier of the polyoxyethylene dodecylphenol ether type were mixed together to obtain an emulsifiable concentrate containing 10% of the active ingredient. In application, the emulsifiable concentrate was diluted with water, and the resulting emulsion was sprayed.

Preparation Example 5

Granule

5 Parts of the compound (9), 93.5 parts of clay and 1.5 parts of a binder of the polyvinyl alcohol type were thoroughly pulverized and mixed together, kneaded with water and then granulated and dried to obtain a granule containing 5% of the active ingredient. In application, the granule was applied as it is or may be mixed with soil.

Preparation Example 6

Floating type granule

10 Parts of the compound (10) is sprayed on 85 parts of pumice having an adjusted particle size of 16 to 32 mesh to allow the compound to soak into the pumice. Thereafter, 5 parts of liquid paraffin is further sprayed thereon to obtain a floating type granule containing 10% of active ingredient. In application, the granule was applied as it is.

Preparation Example 7

Coating type granule

10 Parts of the compound (13) is sprayed on 77 parts of silica sand having an adjusted particle size of 16 to 32 mesh, and then 3 parts of a 10% aqueous polyvinyl alcohol solution is further sprayed thereon. The mixture is blended with 10 parts of white carbon to obtain a coating type granule containing 10% of active ingredient. In application, the granule was applied as it is.

Preparation Example 8

Granule

10 Parts of the compound (14), 30 parts of bentonite, 1 part of calcium lignosulfonate, 0.1 part of sodium laurylsulfate and 58.9 parts of clay are mixed. The mixture is kneaded with the addition of water, granulated through a screen of 7 mm. in mesh size and dried. Thus, a granule containing 10% of active ingredient is obtained. In application, the granule may be applied as it is or in the form of aqueous dilute solution.

Preparation Example 9

Water-surface-spreading oil-based liquid

1 Part of the compound (4), 10 parts of polyoxypropylene glycol monoether and 89 parts of kerosene are mixed to obtain a water-surface-spreading oil-based liquid containing 1% of active ingredient. In application, the liquid was applied as it is.

Some of the test results which support the fungicidal effects of the 1,8-disubstituted carbostyril derivatives (I) are shown in the following Test Examples wherein part(s) are by weight. In these Text Examples the numbers of the compounds according to this invention correspond to those as shown in Table 1, while the numbers of the known compounds for comparison correspond to those as shown in the following Table 2.

TABLE 2

| Compound No. | Chemical structure | Literature |
|---|---|---|
| i | 1-methyl-quinolin-2(1H)-one | U.S. Pat. No. 3,836,657 |
| ii | 4-methyl-1-ethyl-8-methyl-quinolin-2(1H)-one | U.S. Pat. No. 3,836,657 |
| iii | 4-methyl-1-methyl-7-methyl-quinolin-2(1H)-one | U.S. Pat. No. 3,836,657 |
| iv | 1-ethyl-8-methyl-quinolin-2(1H)-one | U.S. Pat. No. 3,836,657 |
| v | 4-methyl-1-methyl-quinolin-2(1H)-one | U.S. Pat. No. 3,836,657; Japanese Patent Publication (unexamined) No. 50136/1974 |
| vi | 4-chloro-1-methyl-quinolin-2(1H)-one | U.S. Pat. No. 3,879,553 |
| vii | 4-methyl-1-ethyl-8-methyl-quinoline-2(1H)-thione | U.S. Pat. No. 3,836,657 |
| viii | 4-methyl-1-methyl-7-methyl-quinoline-2(1H)-thione | U.S. Pat. No. 3,836,657 |
| ix | 4-methyl-1-methyl-quinoline-2(1H)-thione | U.S. Pat. No. 3,836,657 |
| x | 4-methyl-1-ethyl-quinoline-2(1H)-thione | U.S. Pat. No. 3,836,657 |

EXAMPLE 1

Rice Blast Controlling Effec—Foliar Application (Preventive Effect)

To rice plants (Kinki No. 33, 4–5 leaves stage) cultivated in pots of 9 cm. in diameter, test compounds in the form of emulsifiable concentrates prepared according to the method described in Preparation Example 4 were diluted with water and spray-applied by means of spray gun in an amount of 15 ml/pot. After one day from said spraying, a spore suspension of Pyricularia oryzae was spray-inoculated onto the plants and the inoculated pots were placed in a constant temperature room maintained at 24°–26° C. and a humidity of more than 90%. After 4 days standing, disease severity was determined by the percentage of infected leaf area and examined the control effect. The results are shown in the following Table 3. Disease control was calculated by using the following equation.

$$\text{Disease severity} = \frac{\Sigma(\text{infection index} \times \text{number of leaves})}{8 \times \text{total number of leaves observed}} \times 100$$

| infection index | % of leaf area infected |
|---|---|
| 0 | 0% (none) |
| 1 | less than 10% |
| 2 | 10% to less than 25% |
| 4 | 25% to less than 55% |
| 8 | 55% to 100% |

$$\text{Disease control (\%)} = \left(1 - \frac{\text{disease severity in treated plot}}{\text{disease severity in untreated plot}}\right) \times 100$$

TABLE 3

| Test compound No. | Concentration of active ingredient (ppm) | Disease control (%) |
|---|---|---|
| 1 | 100 | 100 |
| 2 | " | " |
| 3 | " | " |
| 4 | " | " |
| 5 | " | " |
| 6 | " | " |
| 7 | " | " |
| 8 | " | " |
| 9 | " | " |
| 10 | " | " |
| 11 | " | " |

TABLE 3-continued

| Test compound No. | Concentration of active ingredient (ppm) | Disease control (%) |
|---|---|---|
| 12 | " | " |
| 13 | " | " |
| 14 | " | " |
| 15 | " | " |
| 16 | " | " |
| i | " | 10 |
| ii | " | 50 |
| iii | " | 0 |
| iv | " | 54 |
| v | " | 70 |
| vi | " | 60 |
| vii | " | 50 |
| viii | " | 0 |
| ix | " | 65 |
| x | " | 20 |
| Commercial fungicide* | " | 85 |
| Untreated | — | 0 |

*O,O-diisopropyl S-benzyl phosphorothiolate (48% E.C.)

EXAMPLE 2
Rice Blast Controlling Effect—Foliar Application (Residual Effect)

To rice plants (Kinki No. 33, 4–5 leaves stage) cultivated in pots of 9 cm. in diameter, test compounds in the form of emulsifiable concentrates prepared as in Preparation example 4 were diluted with water and applied by means of spray gun in an amount of 15 ml. per pot. After 4 days from said spraying, a spore suspension of *Pyricularia oryzae* was spray-inoculated onto the plants and the inoculated pots were placed in a constant temperature room maintained at 24°–26° C. and a humidity of more than 90%. After 4 days standing, disease severity was determined by the percentage of infected leaf area and examined control effects of the tested compounds. The results are shown in the following Table 4. The calculation of disease severity and of control % were carried out as in Example 1.

TABLE 4

| Test compound No. | Concentration of active ingredient (ppm) | Disease control (%) |
|---|---|---|
| 1 | 500 | 100 |
| 2 | " | " |
| 3 | " | " |
| 4 | " | " |
| 5 | " | " |
| 6 | " | " |
| 7 | " | " |
| 8 | " | " |
| 9 | " | " |
| 10 | " | " |
| 11 | " | " |
| 12 | " | " |
| 13 | " | " |
| 14 | " | " |
| 15 | " | " |
| 16 | " | " |
| i | " | 0 |
| ii | " | 10 |
| iii | " | 0 |
| iv | " | 10 |
| v | " | 20 |
| vi | " | 10 |
| vii | " | 10 |
| viii | " | 0 |
| ix | " | 20 |
| x | " | 0 |
| Commercial fungicide* | " | 40 |
| Untreated | — | 0 |

*O-ethyl S,S-diphenyl dithiophosphate (30% E.C.)

EXAMPLE 3
Rice Blast Controlling Effect—Submerged Application

To rice plants (Kinki No. 33, 5–6 leaves stage) cultivated under flooded conditions in Wagner pots (1/5000 are), test compounds formulated in granules as in Preparation example 5 were submerged-applied. The test granules were scattered uniformly on the surface of water in an amount equivalent to 500 g. of active ingredient per 10 ares, and the pots were maintained at a depth of 4–5 cm. for defined period of time before inoculation with test microorganisms, in a green house. After 4 days and 30 days from said medication, a spore suspension of *Pyricularia oryzae* was spray-inoculated onto the plants and the inoculated pots were placed in a constant temperature room maintained at 24°–26° C. and a humidity of more than 90%. After 4 days standing, disease severity was examined by observing the percentage of infected leaf area and determined the control effects as in Example 1. The results are shown in the following Table 5.

TABLE 5

| Test compound No. | Disease control (%) | |
|---|---|---|
| | Treated at 4 days before inoculation | Treated at 30 days before inoculation |
| 1 | 100 | 100 |
| 2 | " | 100 |
| 3 | " | 85 |
| 4 | " | 100 |
| 5 | " | 100 |
| 6 | " | 100 |
| 7 | " | 100 |
| 8 | " | 100 |
| 9 | " | 100 |
| 10 | " | 100 |
| 11 | " | 100 |
| 12 | " | 100 |
| 13 | " | 100 |
| 14 | " | 100 |
| 15 | " | 100 |
| 16 | " | " |
| i | 0 | 0 |
| ii | 40 | 5 |
| iii | 0 | 0 |
| iv | 50 | 10 |
| v | 70 | 5 |
| vi | 45 | 0 |
| vii | 40 | 0 |
| viii | 0 | 0 |
| ix | 70 | 10 |
| x | 20 | 0 |
| Commercial fungicide* | 90 | 20 |
| Untreated | 0 | 0 |

*O,O-diisopropyl S-benzyl phosphorothiolate (17% granule)

EXAMPLE 4
Rice Blast Controlling Effect—Soil Application Test

To rice plants (Kinki No. 33, 5–6 leaves stage) cultivated in Wagner pots (1/5000 are), test compounds in the form of emulsifiable concentrates formulated as in Preparation example 4 were applied to soil. Each emulsifiable concentrate was diluted with water and applied on the surface of soil in an amount equivalent to 500 g. active ingredient per 10 ares. After 4 days and 30 days, a spore suspension of *Pyricularia oryzae* was spray-inoculated onto the plant and the inoculated pots were placed in a constant temperature room maintained at 24°–26° C. and a humidity of more than 90%. After 4 days standing, disease severity and control effect were determined as in Example 1. The results are shown in the following Table 6.

TABLE 6

| Test compound No. | Disease control (%) | |
|---|---|---|
| | Treated at 4 days before inoculation | Treated at 30 days before inoculation |
| 1 | 100 | 100 |
| 2 | " | " |
| 3 | " | 80 |
| 4 | " | 100 |
| 5 | " | 98 |
| 6 | " | 95 |
| 7 | " | 100 |
| 8 | " | " |
| 9 | " | " |
| 10 | " | " |
| 11 | " | " |
| 12 | " | " |
| 13 | " | " |
| 14 | " | 85 |
| 15 | " | 100 |
| 16 | " | " |
| i | 0 | 0 |
| ii | 45 | 0 |
| iii | 0 | 0 |
| iv | 60 | 5 |
| v | 75 | 5 |
| vi | 50 | 0 |
| vii | 40 | 0 |
| viii | 0 | 0 |
| ix | 70 | 5 |
| x | 20 | 5 |
| Commercial fungicide* | 95 | 15 |
| Untreated | 0 | 0 |

*O,O-diisopropyl S-benzylphosphorothiolate (48% E.C.)

EXAMPLE 5

Rice Blast Controlling Effect—Transplant Flat Application Test

To rice plant (Kinki No. 33, 2–2.5 leaves stage) cultivated in a 30×60×3 cm. transplant flat, test compounds formulated in granules as in Preparation example 5 were applied to soil. The test granules were scattered uniformly over the soil surface in an amount equivalent to 20 g., of active ingredient per transplant flat. After 24 hours, treated plants were removed from the flats by cutting 1 cm² blocks of soil and hand transplanting roots plus soil into flooded conditions in Wagner pots (1/5000 are). The pots were maintained at a depth of 4–5 cm. for defined period of time before inoculation with test microorganisms, in green house. After 60 days from said medication, a spore suspension of *Pyricularia oryzae* was spray-inoculated onto the plants and the inoculated pots were placed in a constant temperature room maintained at 24°–26° C. and a humidity of more than 90%. After 4 days standing, disease severity was examined by observing the percentage of infected leaf area and determined the control effects as in Example 1. The results are shown in the following Table 7.

TABLE 7

| Test compound No. | Disease control (%) |
|---|---|
| 1 | 100 |
| 2 | " |
| 3 | 85 |
| 4 | 100 |
| 5 | 99 |
| 6 | 97 |
| 7 | 100 |
| 8 | 100 |
| 9 | 100 |
| 10 | 100 |
| 11 | 100 |

TABLE 7-continued

| Test compound No. | Disease control (%) |
|---|---|
| 12 | 100 |
| 13 | 100 |
| 14 | 90 |
| 15 | 100 |
| 16 | 100 |
| i | 0 |
| ii | 0 |
| iii | 0 |
| iv | 5 |
| v | 5 |
| vi | 0 |
| vii | 0 |
| viii | 0 |
| ix | 5 |
| x | 0 |
| Commercial fungicide* | 20 |
| Untreated | 0 |

*O,O-diisopropyl S-benzyl phosphorothiolate (17% granule)

What is claimed is:

1. A method of controlling the fungus *Pyricularia oryzae*, which comprises applying a fungicidally effective amount against *Pyricularia oryzae* of a compound of the formula

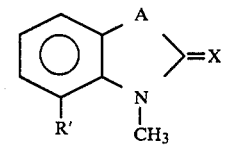

wherein X is an oxygen or sulfur atom, A is an ethylene or a vinylene group, R' is a chlorine, bromine or fluorine atom or methyl group.

2. A composition for controlling the fungus *Pyricularia oryzae* which comprises an effective amount to combat said fungus of a compound of the formula:

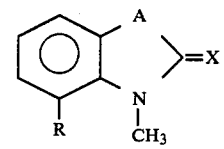

wherein X is an oxygen or sulfur atom, A is an ethylene or a vinylene group, R' is a chlorine, bromine or fluorine atom or methyl group; provided that R' is a chlorine, bromine or fluorine atom when X is an oxygen atom and A is a vinylene group, and a carrier or inert diluent.

3. The fungicidal composition according to claim 2 wherein R' is a chlorine, bromine or fluorine atom, A is a vinylene group and X is an oxygen atom.

4. The fungicidal composition according to claim 2 wherein R' is a chlorine, bromine or fluorine atom or methyl group, A is an ethylene group and X is an oxygen atom.

5. The fungicidal composition according to claim 2 wherein R' is a chlorine, bromine or fluorine atom or methyl group, A is an ethylene or vinylene group and X is a sulfur atom.

6. The fungicidal composition according to claim 2 wherein R' is a chlorine atom, A is vinylene group and X is an oxygen atom.

7. The fungicidal composition according to claim 2 wherein R' is a chlorine atom, A is an ethylene group and X is an oxygen atom.

8. The fungicidal composition according to claim 2 wherein R' is a methyl group, A is an ethylene group and X is an oxygen atom.

9. The fungicidal composition according to claim 2 wherein R' is a chlorine atom, A is a vinylene group and X is sulfur atom.

10. The fungicidal composition according to claim 2 wherein R' is a chlorine atom, A is an ethylene group and X is a sulfur atom.

11. The fungicidal composition according to claim 2 wherein R' is a chlorine atom, A is an ethylene group and X is a sulfur atom.

12. The fungicidal composition according to claim 2 wherein R' is a methyl group, A is an ethylene group and X is a sulfur atom.

* * * * *